(12) United States Patent
Ryba et al.

(10) Patent No.: US 9,017,317 B2
(45) Date of Patent: Apr. 28, 2015

(54) REFRIGERANT SUPPLY SYSTEM FOR CRYOTHERAPY INCLUDING REFRIGERANT RECOMPRESSION AND ASSOCIATED DEVICES, SYSTEMS, AND METHODS

(71) Applicant: Medtronic Ardian Luxembourg S.a.r.l., Luxembourg (LU)

(72) Inventors: Eric Ryba, Durango, CO (US); Gary Kelly, Santa Rosa, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 201 days.

(21) Appl. No.: 13/707,385

(22) Filed: Dec. 6, 2012

(65) Prior Publication Data
US 2014/0163538 A1   Jun. 12, 2014

(51) Int. Cl.
*A61B 18/18* (2006.01)
*A61B 18/02* (2006.01)
*A61F 7/00* (2006.01)
(Continued)

(52) U.S. Cl.
CPC .............. *A61B 18/02* (2013.01); *A61F 7/0085* (2013.01); *A61F 7/12* (2013.01); *A61B 2018/00648* (2013.01); *A61B 2018/00672* (2013.01); *A61B 2018/00744* (2013.01); *A61B 2018/00863* (2013.01); *A61B 2018/0212* (2013.01); *A61B 2018/0262* (2013.01);
(Continued)

(58) Field of Classification Search
CPC ............................ A61B 18/02; A61B 2018/02
USPC .......................................................... 606/21
See application file for complete search history.

(56) References Cited

U.S. PATENT DOCUMENTS 3,125,096 A   3/1964 Antiles et al.
3,298,371 A   1/1967 Lee
(Continued)

FOREIGN PATENT DOCUMENTS

DE   4406451   9/1995
EP   0655225   5/1995
(Continued)

OTHER PUBLICATIONS

International Search Report and Written Opinion for International App. No. PCT/US2013/073177, mailed Jun. 27, 2014, 21 pages.
(Continued)

*Primary Examiner* — Robert N Wieland

(57) ABSTRACT

Cryotherapeutic systems configured for refrigerant recompression and associated devices, systems, and methods are disclosed herein. A cryotherapeutic system configured in accordance with a particular embodiment includes a high-pressure line, a low-pressure line, a recompression unit, and a cryo-catheter. The recompression unit increases the pressure of refrigerant from the low-pressure line to the high-pressure line to a treatment pressure sufficient for cryogenic alteration of tissue. The high-pressure line and the low-pressure line include, respectively, a first connector and a second connector. The cryo-catheter includes a shaft, a supply lumen in the shaft that is coupled to the first connector, an exhaust lumen in the shaft that is coupled to the second connector, and a cryo-applicator attached to the shaft having a cooling chamber configured to receive refrigerant from the supply lumen and to return refrigerant via the exhaust lumen to the low-pressure line.

25 Claims, 3 Drawing Sheets

(51) Int. Cl.
*A61F 7/12* (2006.01)
*A61B 18/00* (2006.01)

(52) U.S. Cl.
CPC *A61B 2018/0275* (2013.01); *A61F 2007/0056* (2013.01); *A61F 2007/126* (2013.01)

(56) References Cited

U.S. PATENT DOCUMENTS

| | | | |
|---|---|---|---|
| 3,901,241 A | 8/1975 | Allen, Jr. | |
| 3,924,628 A | 12/1975 | Droegemueller et al. | |
| 4,275,734 A | 6/1981 | Mitchiner | |
| 4,602,624 A | 7/1986 | Naples et al. | |
| 4,649,936 A | 3/1987 | Ungar et al. | |
| 4,709,698 A | 12/1987 | Johnston et al. | |
| 4,764,504 A | 8/1988 | Johnson et al. | |
| 4,976,711 A | 12/1990 | Parins et al. | |
| 5,108,390 A | 4/1992 | Potocky et al. | |
| 5,190,539 A | 3/1993 | Fletcher et al. | |
| 5,300,068 A | 4/1994 | Rosar et al. | |
| 5,308,323 A | 5/1994 | Sogawa et al. | |
| 5,334,181 A | 8/1994 | Rubinsky et al. | |
| 5,342,301 A | 8/1994 | Saab | |
| 5,358,514 A | 10/1994 | Schulman et al. | |
| 5,368,591 A | 11/1994 | Lennox et al. | |
| 5,383,856 A | 1/1995 | Bersin | |
| 5,417,355 A | 5/1995 | Broussalian et al. | |
| 5,423,744 A | 6/1995 | Gencheff et al. | |
| 5,425,364 A | 6/1995 | Imran | |
| 5,484,400 A | 1/1996 | Edwards et al. | |
| 5,571,147 A | 11/1996 | Sluijter et al. | |
| 5,588,964 A | 12/1996 | Imran et al. | |
| 5,599,345 A | 2/1997 | Edwards et al. | |
| 5,624,392 A | 4/1997 | Saab | |
| 5,626,576 A | 5/1997 | Janssen | |
| 5,672,174 A | 9/1997 | Gough et al. | |
| 5,688,266 A | 11/1997 | Edwards et al. | |
| 5,700,282 A | 12/1997 | Zabara | |
| 5,707,400 A | 1/1998 | Terry, Jr. et al. | |
| 5,758,505 A | 6/1998 | Dobak, III et al. | |
| 5,772,590 A | 6/1998 | Webster, Jr. | |
| 5,807,391 A | 9/1998 | Wijkamp | |
| 5,837,003 A | 11/1998 | Ginsburg | |
| 5,860,970 A | 1/1999 | Goddard et al. | |
| 5,865,787 A | 2/1999 | Shapland et al. | |
| 5,868,735 A | 2/1999 | Lafontaine | |
| 5,893,885 A | 4/1999 | Webster et al. | |
| 5,902,299 A | 5/1999 | Jayaraman | |
| 5,944,710 A | 8/1999 | Dev et al. | |
| 5,954,719 A | 9/1999 | Chen et al. | |
| 5,971,979 A | 10/1999 | Joye et al. | |
| 5,983,141 A | 11/1999 | Sluijter et al. | |
| 6,004,269 A | 12/1999 | Crowley et al. | |
| 6,009,877 A | 1/2000 | Edwards | |
| 6,012,457 A | 1/2000 | Lesh | |
| 6,024,752 A | 2/2000 | Horn et al. | |
| 6,035,657 A * | 3/2000 | Dobak et al. | 62/293 |
| 6,066,134 A | 5/2000 | Eggers et al. | |
| 6,099,524 A | 8/2000 | Lipson et al. | |
| 6,117,101 A | 9/2000 | Diederich et al. | |
| 6,135,999 A | 10/2000 | Fanton et al. | |
| 6,149,620 A | 11/2000 | Baker et al. | |
| 6,161,048 A | 12/2000 | Sluijter et al. | |
| 6,161,049 A | 12/2000 | Rudie et al. | |
| 6,161,543 A | 12/2000 | Cox et al. | |
| 6,164,283 A | 12/2000 | Lesh | |
| 6,190,356 B1 | 2/2001 | Bersin | |
| 6,219,577 B1 | 4/2001 | Brown, III et al. | |
| 6,224,592 B1 | 5/2001 | Eggers et al. | |
| 6,237,355 B1 | 5/2001 | Li | |
| 6,241,722 B1 | 6/2001 | Dobak et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,283,959 B1 | 9/2001 | Lalonde et al. | |
| 6,290,696 B1 | 9/2001 | Lafontaine | |
| 6,292,695 B1 | 9/2001 | Webster, Jr. et al. | |
| 6,314,325 B1 | 11/2001 | Fitz | |
| 6,322,558 B1 | 11/2001 | Taylor et al. | |
| 6,322,559 B1 | 11/2001 | Daulton et al. | |
| 6,355,029 B1 | 3/2002 | Joye et al. | |
| 6,405,732 B1 | 6/2002 | Edwards et al. | |
| 6,413,255 B1 | 7/2002 | Stern | |
| 6,432,102 B2 | 8/2002 | Joye et al. | |
| 6,451,045 B1 | 9/2002 | Walker et al. | |
| 6,468,297 B1 | 10/2002 | Williams et al. | |
| 6,488,679 B1 | 12/2002 | Swanson et al. | |
| 6,496,737 B2 | 12/2002 | Rudie et al. | |
| 6,497,703 B1 | 12/2002 | Korteling et al. | |
| 6,506,189 B1 | 1/2003 | Rittman, III et al. | |
| 6,514,226 B1 | 2/2003 | Levin et al. | |
| 6,514,245 B1 | 2/2003 | Williams et al. | |
| 6,517,533 B1 | 2/2003 | Swaminathan | |
| 6,522,926 B1 | 2/2003 | Kieval et al. | |
| 6,527,739 B1 | 3/2003 | Bigus et al. | |
| 6,537,271 B1 | 3/2003 | Murray et al. | |
| 6,540,734 B1 | 4/2003 | Newton et al. | |
| 6,542,781 B1 | 4/2003 | Koblish et al. | |
| 6,551,309 B1 | 4/2003 | LePivert | |
| 6,562,034 B2 | 5/2003 | Edwards et al. | |
| 6,575,933 B1 | 6/2003 | Wittenberger et al. | |
| 6,602,247 B2 | 8/2003 | Lalonde | |
| 6,610,083 B2 | 8/2003 | Keller et al. | |
| 6,616,624 B1 | 9/2003 | Kieval | |
| 6,622,731 B2 | 9/2003 | Daniel et al. | |
| 6,635,054 B2 | 10/2003 | Fjield et al. | |
| 6,648,879 B2 | 11/2003 | Joye et al. | |
| 6,666,858 B2 | 12/2003 | Lafontaine | |
| 6,685,648 B2 | 2/2004 | Flaherty et al. | |
| 6,711,444 B2 | 3/2004 | Koblish | |
| 6,736,835 B2 | 5/2004 | Pellegrino et al. | |
| 6,755,823 B2 | 6/2004 | Lalonde | |
| 6,786,901 B2 | 9/2004 | Joye et al. | |
| 6,824,543 B2 | 11/2004 | Lentz | |
| 6,845,267 B2 | 1/2005 | Harrison et al. | |
| 6,850,801 B2 | 2/2005 | Kieval et al. | |
| 6,875,209 B2 | 4/2005 | Zvuloni et al. | |
| 6,885,888 B2 | 4/2005 | Rezai | |
| 6,893,436 B2 | 5/2005 | Woodard et al. | |
| 6,905,510 B2 | 6/2005 | Saab | |
| 6,908,462 B2 | 6/2005 | Joye et al. | |
| 6,923,808 B2 | 8/2005 | Taimisto | |
| 6,939,346 B2 | 9/2005 | Kannenberg et al. | |
| 6,981,382 B2 | 1/2006 | Lentz et al. | |
| 7,060,062 B2 | 6/2006 | Joye et al. | |
| 7,081,112 B2 | 7/2006 | Joye et al. | |
| 7,081,115 B2 | 7/2006 | Taimisto | |
| 7,149,574 B2 | 12/2006 | Yun et al. | |
| 7,156,840 B2 | 1/2007 | Lentz et al. | |
| 7,162,303 B2 | 1/2007 | Levin et al. | |
| 7,221,979 B2 | 5/2007 | Zhou et al. | |
| 7,306,590 B2 | 12/2007 | Swanson | |
| 7,357,797 B2 | 4/2008 | Ryba | |
| 7,381,200 B2 | 6/2008 | Katoh et al. | |
| 7,390,894 B2 | 6/2008 | Weinshilboum et al. | |
| 7,604,631 B2 | 10/2009 | Reynolds | |
| 7,617,005 B2 | 11/2009 | Demarais et al. | |
| 7,641,679 B2 | 1/2010 | Joye et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,758,571 B2 | 7/2010 | Saadat | |
| 7,778,703 B2 | 8/2010 | Gross et al. | |
| 7,785,289 B2 | 8/2010 | Rios et al. | |
| 7,861,725 B2 | 1/2011 | Swanson | |
| 7,972,327 B2 | 7/2011 | Eberl et al. | |
| 8,088,125 B2 | 1/2012 | Lafontaine | |
| 8,131,371 B2 | 3/2012 | Demarals et al. | |
| 8,131,372 B2 | 3/2012 | Levin et al. | |
| 8,140,170 B2 | 3/2012 | Rezai et al. | |
| 8,145,317 B2 | 3/2012 | Demarais et al. | |
| 8,150,518 B2 | 4/2012 | Levin et al. | |
| 8,150,519 B2 | 4/2012 | Demarais et al. | |
| 8,150,520 B2 | 4/2012 | Demarais et al. | |

(56) References Cited

U.S. PATENT DOCUMENTS

| | | |
|---|---|---|
| 8,175,711 B2 | 5/2012 | Demarais et al. |
| 8,473,067 B2 | 6/2013 | Hastings et al. |
| 8,475,441 B2 | 7/2013 | Babkin et al. |
| 8,480,664 B2 | 7/2013 | Watson et al. |
| 8,663,211 B2 | 3/2014 | Fourkas et al. |
| 8,740,895 B2 | 6/2014 | Mayse et al. |
| 8,777,943 B2 | 7/2014 | Mayse et al. |
| 2001/0021847 A1 | 9/2001 | Abboud et al. |
| 2002/0045893 A1 | 4/2002 | Lane et al. |
| 2002/0120258 A1 | 8/2002 | Lalonde |
| 2002/0165532 A1 | 11/2002 | Hill et al. |
| 2002/0183682 A1 | 12/2002 | Darvish et al. |
| 2003/0036752 A1 | 2/2003 | Joye et al. |
| 2003/0050681 A1 | 3/2003 | Pianca et al. |
| 2003/0060762 A1 | 3/2003 | Zvuloni et al. |
| 2003/0060858 A1 | 3/2003 | Kieval et al. |
| 2003/0088240 A1 | 5/2003 | Saadat |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2004/0010289 A1 | 1/2004 | Biggs et al. |
| 2004/0024392 A1 | 2/2004 | Lewis et al. |
| 2004/0215186 A1 | 10/2004 | Cornelius et al. |
| 2005/0080409 A1 | 4/2005 | Young et al. |
| 2005/0187579 A1 | 8/2005 | Danek et al. |
| 2005/0228460 A1 | 10/2005 | Levin et al. |
| 2005/0240117 A1 | 10/2005 | Zvuloni et al. |
| 2006/0084962 A1 | 4/2006 | Joye et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0212027 A1 | 9/2006 | Marrouche et al. |
| 2006/0235375 A1* | 10/2006 | Littrup et al. .................. 606/21 |
| 2006/0247611 A1 | 11/2006 | Abboud et al. |
| 2006/0271111 A1 | 11/2006 | Demarais et al. |
| 2007/0093799 A1* | 4/2007 | Abboud et al. ................. 606/22 |
| 2007/0129720 A1 | 6/2007 | Demarais et al. |
| 2007/0185445 A1 | 8/2007 | Nahon et al. |
| 2007/0265687 A1 | 11/2007 | Deem et al. |
| 2007/0299433 A1 | 12/2007 | Williams et al. |
| 2008/0208182 A1 | 8/2008 | Lafontaine et al. |
| 2008/0300584 A1 | 12/2008 | Lentz et al. |
| 2008/0300586 A1* | 12/2008 | Zvuloni ......................... 606/22 |
| 2008/0306475 A1 | 12/2008 | Lentz et al. |
| 2008/0312644 A1 | 12/2008 | Fourkas et al. |
| 2008/0319513 A1 | 12/2008 | Pu et al. |
| 2009/0036948 A1 | 2/2009 | Levin et al. |
| 2009/0088735 A1 | 4/2009 | Abboud et al. |
| 2009/0182316 A1 | 7/2009 | Bencini |
| 2009/0182317 A1 | 7/2009 | Bencini |
| 2009/0209949 A1 | 8/2009 | Ingle et al. |
| 2009/0281533 A1 | 11/2009 | Ingle et al. |
| 2009/0287202 A1 | 11/2009 | Ingle et al. |
| 2009/0299355 A1 | 12/2009 | Bencini et al. |
| 2010/0049184 A1 | 2/2010 | George et al. |
| 2010/0069900 A1 | 3/2010 | Shirley et al. |
| 2010/0100087 A1 | 4/2010 | Mazzone et al. |
| 2010/0106148 A1 | 4/2010 | Joye et al. |
| 2010/0114269 A1 | 5/2010 | Wittenberger et al. |
| 2010/0125266 A1 | 5/2010 | Deem et al. |
| 2010/0130970 A1 | 5/2010 | Williams et al. |
| 2010/0137860 A1 | 6/2010 | Demarais et al. |
| 2010/0137952 A1 | 6/2010 | Demarais et al. |
| 2010/0179526 A1 | 7/2010 | Lawrence |
| 2010/0179527 A1 | 7/2010 | Watson et al. |
| 2010/0191112 A1 | 7/2010 | Demarais et al. |
| 2010/0198203 A1 | 8/2010 | Kuck et al. |
| 2010/0204687 A1* | 8/2010 | Abboud et al. .................. 606/21 |
| 2010/0222851 A1 | 9/2010 | Deem et al. |
| 2010/0222854 A1 | 9/2010 | Demarais et al. |
| 2010/0234838 A1 | 9/2010 | Watson |
| 2010/0249766 A1 | 9/2010 | Saadat |
| 2010/0256621 A1 | 10/2010 | Babkin et al. |
| 2010/0280507 A1 | 11/2010 | Babkin et al. |
| 2011/0152855 A1 | 6/2011 | Mayse et al. |
| 2011/0263921 A1 | 10/2011 | Vrba et al. |
| 2011/0270238 A1 | 11/2011 | Rizq et al. |
| 2011/0282272 A1 | 11/2011 | Lafontaine |
| 2012/0029509 A1 | 2/2012 | Smith |
| 2012/0029511 A1 | 2/2012 | Smith et al. |
| 2012/0089047 A1 | 4/2012 | Ryba et al. |
| 2012/0123261 A1 | 5/2012 | Jenson et al. |
| 2012/0130289 A1 | 5/2012 | Demarais et al. |
| 2012/0130345 A1 | 5/2012 | Levin et al. |
| 2012/0130360 A1 | 5/2012 | Buckley et al. |
| 2012/0130368 A1 | 5/2012 | Jenson |
| 2012/0136417 A1 | 5/2012 | Buckley et al. |
| 2012/0136418 A1 | 5/2012 | Buckley et al. |
| 2012/0143097 A1 | 6/2012 | Pike, Jr. |
| 2012/0150267 A1 | 6/2012 | Buckley et al. |
| 2012/0172837 A1 | 7/2012 | Demarais et al. |
| 2012/0253336 A1 | 10/2012 | Littrup et al. |
| 2013/0090650 A1 | 4/2013 | Jenson et al. |
| 2013/0123770 A1 | 5/2013 | Smith |
| 2013/0184696 A1 | 7/2013 | Fourkas et al. |
| 2013/0345688 A1 | 12/2013 | Babkin et al. |
| 2014/0046313 A1 | 2/2014 | Pederson et al. |
| 2014/0066914 A1 | 3/2014 | Lafontaine |

FOREIGN PATENT DOCUMENTS

| | | |
|---|---|---|
| EP | 0955012 | 11/1999 |
| EP | 1129670 | 9/2001 |
| EP | 1164963 | 1/2002 |
| EP | 1389477 | 2/2004 |
| EP | 1502553 | 2/2005 |
| EP | 1559362 | 8/2005 |
| EP | 2558016 | 2/2013 |
| EP | 2598070 | 6/2013 |
| EP | 2598071 | 6/2013 |
| EP | 2608837 | 7/2013 |
| GB | 228367 | 2/1925 |
| GB | 1422535 | 1/1976 |
| GB | 2289414 | 11/1995 |
| SU | 718099 | 2/1980 |
| SU | 1153901 | 5/1985 |
| SU | 1329781 | 8/1987 |
| SU | 1378835 | 3/1988 |
| SU | 1771725 | 6/1990 |
| WO | WO-9525472 | 9/1995 |
| WO | WO-9725011 | 7/1997 |
| WO | WO-9736548 | 10/1997 |
| WO | WO-99/00060 | 1/1999 |
| WO | WO-9905979 | 2/1999 |
| WO | WO-9927862 | 6/1999 |
| WO | WO-0122897 | 4/2001 |
| WO | WO-0164145 | 9/2001 |
| WO | WO-0170114 | 9/2001 |
| WO | WO-0200128 | 1/2002 |
| WO | WO-0204042 | 1/2002 |
| WO | WO-0207625 | 1/2002 |
| WO | WO-0207628 | 1/2002 |
| WO | WO-0213710 | 2/2002 |
| WO | WO-02058576 | 8/2002 |
| WO | WO-03020334 | 3/2003 |
| WO | WO-03061496 | 7/2003 |
| WO | WO-2005030072 | 4/2005 |
| WO | WO-2005038357 | 4/2005 |
| WO | WO-2005041748 | 5/2005 |
| WO | WO-0510528 | 11/2005 |
| WO | WO-2006041881 | 4/2006 |
| WO | WO-2006096272 | 9/2006 |
| WO | WO-2006124177 | 11/2006 |
| WO | WO-2007008954 | 1/2007 |
| WO | WO-2008131037 | 10/2008 |
| WO | WO-2011056684 | 5/2011 |
| WO | WO-2011082278 | 7/2011 |
| WO | WO-2011082279 | 7/2011 |
| WO | WO-2012016135 | 2/2012 |
| WO | WO-2012016137 | 2/2012 |
| WO | WO-2012058430 | 5/2012 |

(56) References Cited

FOREIGN PATENT DOCUMENTS

| WO | WO-2013074683 | 5/2013 |
|---|---|---|
| WO | WO-2013106859 | 7/2013 |

OTHER PUBLICATIONS

European Search Report for European Application No. 13159256, Date Mailed: Oct. 17, 2013, 6 pages.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. http://www.cxvascular.com/in-latest-news/interventional-news—latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page, <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced Its Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by vol. expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldH eadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Final Office Action; U.S. Appl. No. 12/827,700; mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.
Gertner, Jon, "Meet The Tech Duo That's Revitalizing The Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Linz, Dominik et al., "Renal denervation suppresses ventricular arrhythmias during acute ventricular ischemia in pigs." Heart Rhythm, vol. 0, No. 0, 2013, 6 pages.
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Millard, F. C., et al, "Renal Embolization for ablation of function in renal failure and hypertension." Postgraduate Medical Journal, 65, 729-734, (1989).
Ormiston, John et al., "First-in-human use of the OneShotTM renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Schlaich, Markus et al., "Renal Denervation in Human Hypertension: Mechanisms, Current Findings, and Future Prospects." Curr Hypertens Rep, vol. 14, 2012, 7 pages.

(56) References Cited

OTHER PUBLICATIONS

Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stouffer, G. A. et al., "Catheter-based renal denervation in the treatment of resistant hypertension." Journal of Molecular and Cellular Cardiology, vol. 62, 2013, 6 pages.
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013.
ClinicalTrials.gov, Renal Denervation in Patients with uncontrolled Hypertension in Chinese (2011), www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Schneider, Peter A., "Endovascular Skills—Guidewire and Catheter Skills for Endovascular Surgery," Second Edition Revised and Expanded, 10 pages, (2003).
Kandarpa, Krishna et al., "Handbook of Interventional Radiologic Procedures", Third Edition, pp. 194-210 (2002).
ThermoCool Irrigated Catheter and Integrated Ablation System, Biosense Webster (2006).
Mount Sinai School of Medicine clinical trial for Impact of Renal Sympathetic Denervation of Chronic Hypertenion, Mar. 2013, http://clinicaltrials.gov/ct2/show/NCT01628198.
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Oz, Mehmet, Pressure Relief, TIME, Jan. 9, 2012, 2 pages. <www.time.come/time/printout/0,8816,2103278,00.html>.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Pulmonary Vein Stenosis Following Catheter Ablation of Atrial Fibrillation, Curr. Opin. Cardio. 20 :484-490, 2005.
Papademetriou, Vasilios, Renal Sympathetic Denervation for the Treatment of Difficult-to-Control or Resistant Hypertension, Int. Journal of Hypertension, 2011, 8 pages.
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardian Electrophysiology, 2001, pp. 401-410.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361;9.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimentla Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implictions for an Old Concept," Hypertension, 2009; 54:1195-1201.
Schlaich, M.P. et al., "Renal Sympathetic-Nerve Ablation for Uncontrolled Hypertension," N. Engl J Med 2009; 361(9): 932-934.
Smithwick, R.H. et al., "Splanchnicectomy for Essential Hypertension," Journal Am Med Assn, 1953; 152:1501-1504.

(56) References Cited

OTHER PUBLICATIONS

Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
USRDS United States Renal Data System 2003 Annual Data Report.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Benito, F., et al. "Radiofrequency catheter ablation of accessory pathways in infants." Heart, 78:160-162 (1997).
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Intery Cardiac Electrophysiol, 2:285-292 (1998).
Gelfand, M., et al., "Treatment of renal failure and hypertension." U.S. Appl. No. 60/442,970, 2003.
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Intery Radio!, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988).
Huang et al., "Renal denervation prevents and reverses hyperinsulinemia-induced hypertension in rats." Hypertension 32 (1998) pp. 249-254.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustgarten, D.L.,et al., "Cryothermal ablation: Mechanism of tissue injury and current experience in the treatment of tachyarrthythmias." Progr Cardiovasc Dis, 41:481-498 (1999).
Medical-Dictionary.com, Definition of "Animal Model," http://medical-dictionary.com (search "Animal Model"), 2005.
Medtronic, Inc., Annual Report (Form 10-K) (Jun. 28, 2011).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).

Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Swartz, J.F., et al., "Radiofrequency endocardial cateheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Weinstock, M., et al., "Renal denervation prevents sodium rentention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012.
510K Summary of CryoGen Cryosurgery System, filed with FDA Jul. 3, 1997-approved Oct. 1, 1997, 1997, 5 pages.
CO2/Gas Composite Regulator, Sep. 6, 2011, 2 pages. <http://www.genuineinnovations.com/composite-regulator.html>.
CryoGen SS&E: HerOption Uterine Cryoblatin Therapy System, filed with FDA Aug. 15, 2000-approved Apr. 20, 2001,1999, 84 pages.
International Search Report and Written Opinion dated Apr. 12, 2012, International Application No. PCT/US2011/057514, 15 pages.
International Search Report and Written Opinion dated Apr. 13, 2012, International Application No. PCT/US2011/057502, 14 pages.
International Search Report and Written Opinion dated Dec. 28, 2011, International Application No. PCT/US2011/057508, 12 pages.
International Search Report and Written Opinion dated Feb. 14, 2012, International Application No. PCT/US2011/057504, 12 pages.
International Search Report and Written Opinion dated Feb. 20, 2012, International Application No. PCT/US2011/057483, 11 pages.
International Search Report and Written Opinion dated Feb. 23, 2012, International Application No. PCT/US2011/057490, 14 pages.
International Search Report and Written Opinion dated Feb. 6, 2012, International Application No. PCT/US2011/057497, 12 pages.
International Search Report and Written Opinion dated Jun. 13, 2013, International Application No. PCT/US2012/063411, 13 pages.
International Search Report and Written Opinion dated Mar. 16, 2012, International Application No. PCT/US2011/057511, 16 pages.
International Search Report and Written Opinion dated Mar. 9, 2012, International Application No. PCT/US2011/057523, 15 pages.
Lura Harrison, Ph.D. et al., "Cryosurgical Ablation of the A-V Node-His Bundle—A New Method for Producing A-V Block," Circulation, vol. 55, 1977 pp. 463-470.
Medical Grade Gas Dispenser, Sep. 6, 2011, 1 page, <http://www.abd-inc.com/Frame-904990-page1namepage904990.html?refresh=1205442262133>.
Sesia G. et al., "The use of nitrous oxide as a freezing agent in cryosurgery of the prostate," International Surgery [Int Surg], vol. 53, 1970, pp. 82-90.
Special Order Only Thermal Dilution Injector, Obsolete Product, Sep. 6, 2011, 1 page, <http://www.abd-inc.com/Frame-904990-page1nannepage904990.html?refresh=1205442262133>.
Torre, Douglas, MD, "Alternate Cryogens for Cryosurgery," J. Derm. Surgery, Jun. 1975, pp. 56-58.
Voityna SV, "Cryocatheter-tourniquet," Meditsinskaia Tekhnika [Med Tekh], vol. 6, 1976, pp. 47-48.
Beale et al., "Minimally Invasive Treatment for Varicose Veins: A Review of Endovenous Laser Treatment and Radiofrequency Ablation". Lower Extremity Wounds 3(4), 2004, 10 pages.

(56) References Cited

OTHER PUBLICATIONS

Miller, Reed, "Finding A Future for Renal Denervation With Better Controlled Trials." Pharma & Medtech Business Intelligence, Article # 01141006003, Oct. 6, 2014, 4 pages.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Doumas, Michael et al., "Renal Nerve Ablation for Resistant Hypertension: The Dust Has Not Yet Settled." The Journal of Clinical Hypertension. 2014; vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

International Search Report and Written Opinion for International Application No. PCT/US2011/046845, mailed Dec. 16, 2011, 16 pages.

\* cited by examiner

REFRIGERANT SUPPLY SYSTEM FOR CRYOTHERAPY INCLUDING REFRIGERANT RECOMPRESSION AND ASSOCIATED DEVICES, SYSTEMS, AND METHODS

TECHNICAL FIELD

The present technology is related to cryotherapy (e.g., cryoablation). In particular, some embodiments are related to cryotherapeutic systems configured for refrigerant recompression, refrigerant supply devices for cryotherapeutic systems, and cryotherapeutic methods including refrigerant recompression, among other devices, systems, and methods useful in the context of cryotherapy.

BACKGROUND

Many cryotherapeutic procedures include introducing a cryo-catheter into a patient (e.g., into the vasculature of a patient) and cooling a cryo-applicator of the cryo-catheter using refrigerant. In some cases, refrigerant introduced into the cryo-catheter is chilled and circulated through the cryo-applicator without expanding significantly. For example, the cryo-catheter can be thermally insulated proximal to the cryo-applicator such that chilled refrigerant circulated through the cryo-catheter does not readily absorb heat from nearby tissue until it reaches the cryo-applicator. In other cases, refrigerant, which can be chilled or not chilled, expands significantly within the cryo-catheter and drops in temperature and/or absorbs heat from nearby tissue due to the Joule-Thomson effect alone or in combination with increasing latent heat. For example, refrigerant can enter the cryo-catheter partially or entirely in liquid phase at high pressure, expand and/or vaporize by passing through an orifice within the cryo-applicator, and then exit the cryo-catheter in gas phase at low pressure. Cooling via refrigerant expansion can be particularly useful in relatively long and narrow cryo-catheters (e.g., most intravascular cryo-catheters). In such cryo-catheters, for example, refrigerant cooling potential in the form of high refrigerant pressure can usually be maintained more readily than refrigerant cooling potential in the form of low refrigerant temperature while refrigerant is en route to a distal cryo-applicator.

In conventional cryotherapeutic systems configured for cooling by refrigerant expansion, resulting expanded refrigerant is typically exhausted to the atmosphere or collected for disposal. For example, a conventional cryotherapeutic system can be configured to be connected to a hospital scavenging system that transports expanded refrigerant to a centralized location for disposal. Both releasing expanded refrigerant into the atmosphere and transporting expanded refrigerant to a centralized location deplete the supply of refrigerant available to the system. Accordingly, conventional cryotherapeutic systems are typically configured to be connected to refrigerant supply tanks that must frequently be replaced or recharged. Replacing or recharging refrigerant supply tanks, however, can be logistically challenging and costly. Furthermore, although larger refrigerant supply tanks often require replacement or recharging less frequently than smaller refrigerant supply tanks, larger refrigerant supply tanks are also typically more obtrusive and cumbersome to handle than smaller refrigerant supply tanks.

Conventional cryotherapeutic systems are usually only compatible with certain types of refrigerants. For example, many conventional cryotherapeutic systems are configured for use with nitrous oxide, which can be released into the atmosphere or collected for disposal with little or no concern for toxicity or environmental impact. While nitrous oxide is a useful refrigerant, other refrigerants can have more advantageous thermodynamic properties (e.g., greater latent heats of vaporization) than nitrous oxide. These other refrigerants, however, are potentially more harmful to the environment than nitrous oxide. Intentionally and non-incidentally releasing and/or disposing of such refrigerants is, in many cases, prohibited by regulations, inconsistent with accepted medical protocols, or both. Thus, many potentially useful types of refrigerants are not available for use in conventional cryotherapeutic systems configured to release expanded refrigerant into the atmosphere or to collect expanded refrigerant for disposal. This can limit the performance of such systems.

For the reasons stated above and for other reasons, whether or not expressly disclosed herein, there is a need for innovation in the field of cryotherapy. For example, there is a need for innovation with regard to devices, systems, and methods that reduce the need for replacing or recharging refrigerant supply tanks, that facilitate the use of additional types of refrigerants, and/or that have other advantages relative to conventional devices, systems, and/or methods.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Specific details of several embodiments of the present technology are described herein with reference to FIGS. 1-11. Although many of the embodiments are described herein with respect to devices, systems, and methods for intravascular cryotherapeutic neuromodulation, other applications and other embodiments in addition to those described herein are within the scope of the present technology. For example, some embodiments may be useful for intraluminal cryotherapy, extravascular cryotherapy, or intravascular cryotherapy for a purpose other than neuromodulation. It should be noted that some embodiments of the present technology can have different configurations and/or procedures than those shown or described herein. Moreover, a person of ordinary skill in the art will understand that some embodiments of the present technology can have features, components, and/or operations in addition to those shown or described herein and that these and other embodiments can be without several of the features, components, and/or operations shown or described herein without deviating from the present technology.

Cryotherapeutic systems and associated devices, systems, and methods configured in accordance with embodiments of the present technology can have one or more advantageous features relative to the prior art. For example, a cryotherapeutic system in accordance with an embodiment of the present technology can be configured to reuse refrigerant rather than releasing refrigerant into the atmosphere or collecting refrigerant for disposal. The cryotherapeutic system can be configured to collect refrigerant from an exhaust lumen of a cryocatheter, to recompress collected refrigerant, and to supply recompressed refrigerant to a supply lumen of the cryo-catheter or to the supply lumen of another cryo-catheter. In some embodiments, recompressing collected refrigerant includes condensing collected refrigerant such that recompressed refrigerant can be supplied to the supply lumen at least partially in liquid phase. Since refrigerant within the system is reused instead of released into the atmosphere or otherwise discarded outside of the system, the need to replace or recharge a supply tank can be mostly or entirely eliminated. Thus, long-term operation of the system can be less logistically challenging and/or less costly than long-term operation of many conventional cryotherapeutic systems. Furthermore, in some cases, since refrigerant can be generally contained within the system, the system can be used with types of refrigerants that are potentially more harmful to the environment than nitrous oxide, but that also have more advantageous thermodynamic properties than nitrous oxide. For example, in addition to nitrous oxide, the system can be used with suitable hydrofluorocarbons (e.g., difluoromethane), among other types of refrigerants.

Figure 1:
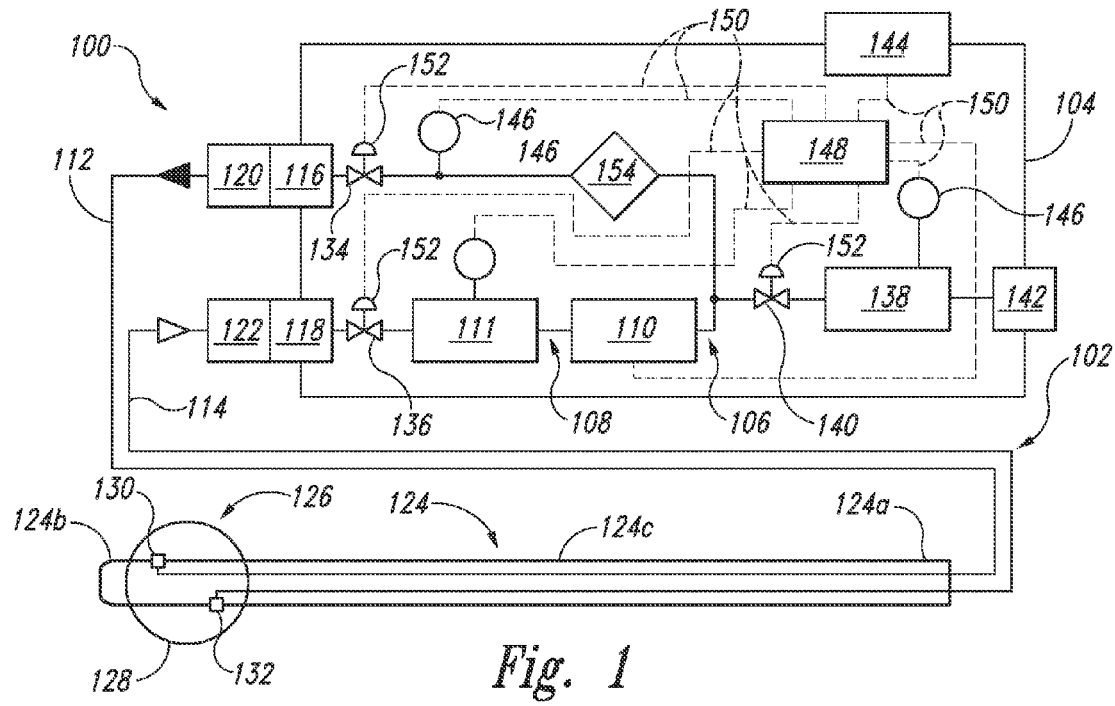
FIGS. 1 and 2 are partially schematic diagrams illustrating cryotherapeutic systems in accordance with embodiments of the present technology.

FIG. 1 is a partially schematic diagram illustrating a cryotherapeutic system 100 in accordance with an embodiment of the present technology. The system 100 can include a cryo-catheter 102 removably connected to a console 104. Within the console 104, the system 100 can include a high-pressure line 106, a low-pressure line 108, and a recompression unit 110 therebetween. In some embodiments, the low-pressure line 108 includes an exhaust vessel 111 configured to contain exhausted refrigerant from the cryo catheter 102. The exhaust vessel 111 can have a volume, for example, from about 3 liters to about 20 liters, from about 5 liters to about 15 liters, or within another suitable range. For example, the volume can be about 10 liters. Instead of or in addition to the exhaust vessel 111, the system 100 can include one or more other components configured for storing refrigerant when the refrigerant is not in use. For example, the high-pressure line 106 can include a supply vessel (not shown) configured to store compressed refrigerant (e.g., liquid refrigerant) downstream from the recompression unit 110.

The high-pressure line 106 can be configured to be operably connected to a supply lumen 112 of the cryo-catheter 102. Similarly, the low-pressure line 108 can be configured to be operably connected to an exhaust lumen 114 of the cryo-catheter 102. For example, the high-pressure line 106 and the low-pressure line 108 can include, respectively, a first coupler 116 and a second coupler 118 accessible from outside the console 104. The first coupler 116 can be configured to cooperatively engage a third coupler 120 of the supply lumen 112. The second coupler 118 can be configured to cooperatively engage a fourth coupler 122 of the exhaust lumen 114. The first and third couplers 116, 120 and the second and fourth couplers 118, 122 can be threaded, compression fit, barbed, or have other suitable cooperative features configured to form releasable fluidic connections. In other embodiments, the cryo-catheter 102 can be permanently connected to the console 104. For example, the first, second, third, and fourth couplers 116, 118, 120, 122 can be eliminated, and the high-pressure line 106 and the low-pressure line 108 can be integral extensions of the supply lumen 112 and the exhaust lumen 114, respectively. In still other embodiments, the first, second, third, and fourth couplers 116, 118, 120, 122 can have other suitable locations within the system 100 (e.g., separate from the console 104).

The cryo-catheter 102 can include an elongated shaft 124 having a proximal end portion 124a, a distal end portion 124b, and a main portion 124c therebetween. At or near the distal end portion 124b, the cryo-catheter 102 can include a cryo-applicator 126 attached to the shaft 124. The cryo-applicator 126 can include a cooling chamber 128 configured to receive refrigerant from the high-pressure line 106 via the supply lumen 112 and to return refrigerant to the low-pressure line 108 via the exhaust lumen 114. In some embodiments, the cooling chamber 128 is a balloon configured to compliantly, non-compliantly, and/or semi-compliantly expand when refrigerant is present within the cooling chamber 128. For example, the cooling chamber 128 can be configured to circumferentially expand to span the cross-sectional area of a blood vessel (e.g., a renal artery). Therapeutically effective cooling can be applied to a wall of the blood vessel via the cryo-applicator 126 (e.g., to cause neuromodulation or another desirable cryotherapeutic effect). In other embodiments, the cryo-applicator 126 can be an integral portion of the shaft 124 and/or the cooling chamber 128 can be non-expandable.

The supply lumen 112 and the exhaust lumen 114 can be positioned at least partially within the shaft 124. For example, the supply lumen 112 can extend from the third coupler 120 to the proximal end portion 124a, along the main portion 124c, and to an expansion orifice 130 of the cryo-applicator 126 within the cooling chamber 128. Similarly, the exhaust lumen 114 can extend from the fourth coupler 122 to the proximal end portion 124a, along the main portion 124c, and to an exhaust opening 132 of the cryo-applicator 126 within the cooling chamber 128. Refrigerant at relatively high pressure can flow from the high-pressure line 106, through the supply lumen 112, and to the expansion orifice 130, and then can expand within the cooling chamber 128 to cool the cryo-applicator 126. For example, refrigerant within the supply lumen 112 proximal to the expansion orifice 130 can be at least partially in liquid phase and vaporize at the expansion orifice 130 or elsewhere within the cooling chamber 128 to cool the cryo-applicator 126 by absorbing latent heat. In some cases, additional cooling can occur without phase change due to the Joule-Thomson effect. Expanded refrigerant at relatively low pressure can exit the cooling chamber 128 through the exhaust opening 132 and flow through the exhaust lumen 114 to the low-pressure line 108.

The console 104 can be configured to regulate the flow of refrigerant into the supply lumen 112 and/or out of the exhaust lumen 114, both of which can affect cooling activity within the cryo-applicator 126. In some embodiments, the high-pressure line 106 includes a supply valve 134 configured to open and close and thereby start and stop the flow of refrigerant toward the supply lumen 112. Similarly, the low-pressure line 108 can include an exhaust valve 136 configured to open and close and thereby start and stop the flow of refrigerant toward the recompression unit 110. The supply valve 134 and the exhaust valve 136 can also be configured to be partially open so as to vary the flow of refrigerant incrementally and/or infinitely within suitable ranges. In many cases, however, it can be advantageous to control the flow of refrigerant primarily or entirely via operation of the recompression unit 110. The recompression unit 110 can be operably connected to the high-pressure line 106 and the low-pressure line 108 and configured to increase the pressure of refrigerant moving from the low-pressure line 108 to the high-pressure line 106. In some cases, refrigerant moving through the recompression unit 110 at least partially condenses. In other cases, refrigerant moving through the recompression unit 110 can enter and exit the recompression unit 110 in the gas phase.

The high-pressure line 106, the low-pressure line 108, and the recompression unit 110 can be configured to define a portion of a closed loop when the high-pressure line 106 is operably connected to the supply lumen 112 and the low-pressure line 108 is operably connected to the exhaust lumen 114. The closed loop, for example, can extend between the recompression unit 110 and the cooling chamber 128 with a high-pressure portion on one side of the closed loop and a low-pressure portion on the other side of the closed loop. The high-pressure portion can include the high-pressure line 106 and the supply lumen 112, and the low-pressure portion can include the low-pressure line 108 and the exhaust lumen 114. In some embodiments, the high-pressure line 106, the supply lumen 112, and any other suitable components within the high-pressure portion are configured to carry liquid refrigerant. Similarly, the low-pressure line 108, the exhaust lumen 114, and any other suitable components within the low-pressure portion can be configured to carry gaseous refrigerant. For example, the cross-sectional area of refrigerant-carrying components along the low-pressure portion can be greater than the cross-sectional area of refrigerant-carrying components along the high-pressure portion to accommodate the greater volume of gaseous refrigerant relative to liquid refrigerant.

The high-pressure line 106, the low-pressure line 108, and the recompression unit 110 can be configured to contain a first volume of refrigerant. In some embodiments, the system 100 is configured to replenish the first volume of refrigerant to account for refrigerant loss (e.g., incidental refrigerant loss) from the first volume of refrigerant. For example, the system 100 can include a make-up reservoir 138 operably connected to the high-pressure line 106. The make-up reservoir 138 can be configured to contain a second volume of refrigerant sufficient to replace refrigerant loss (e.g., incidental refrigerant loss) from the first volume of refrigerant. Such refrigerant loss can occur, for example, when the supply lumen 112 is disconnected from the high-pressure line 106, when the exhaust lumen 114 is disconnected from the low-pressure line 108, or both (e.g., during exchange of the cryo-catheter 102). In some embodiments, the second volume of refrigerant is sufficient to replace refrigerant loss during use of the system 100 for a number of treatments (e.g., a number of cryotherapeutic renal neuromodulation treatments) from about 20 to about 1000, from about 40 to about 500, from about 60 to about 300, or within another suitable range. For example, the second volume of refrigerant can be sufficient to replace refrigerant loss during use of the system 100 for about 100 treatments.

The system 100 can include a make-up valve 140 operably connected to the closed loop at the high-pressure line 106. In other embodiments, the make-up reservoir 138 and the make-up valve 140 can be connected to the closed loop at another suitable point (e.g., at the low-pressure line 108 or at the recompression unit 110). The make-up valve 140 can be configured to regulate the flow of refrigerant from the second volume of refrigerant toward the first volume of refrigerant. For example, the make-up valve 140 can open as needed to replenish the first volume of refrigerant in response to refrigerant loss. Less frequently, the second volume of refrigerant can be replenished via a make-up port 142 of the system 100, which can be accessible from outside the console 104. In some cases, the console 104 alone or together with the cryo-catheter 102 can be provided to a user pre-filled with a suitable refrigerant (e.g., nitrous oxide or a hydrofluorocarbon refrigerant). In other cases, a service technician can introduce an initial charge of refrigerant (e.g., via the make-up port 142) when the system 100 is first installed.

The system 100 can be configured for manual or automatic control. For example, the supply valve 134, the exhaust valve 136, and the make-up valve 140 can be operated manually or automatically. In some embodiments, the system 100 includes a user interface 144, one or more sensors 146, a controller 148, and communication lines 150 operably connecting the user interface 144 and the sensors 146 to the controller 148. The system 100 can further include one or more actuators 152 operably connected to the supply valve 134, the exhaust valve 136, and/or the make-up valve 140 individually. The actuators 152 and the recompression unit 110 can be operably connected to the controller 148 via the communication lines 150. In other embodiments, some or all of the communication lines 150 can be eliminated and the user interface 144, the sensors 146, the actuators 152, and/or the recompression unit 110 can be configured to communicate with the controller 148 wirelessly. The controller 148 can include a processor (not shown) and memory (also not shown) and can be programmed with instructions (e.g., non-transitory instructions) corresponding to one or more suitable control algorithms. For example, the controller 148 can be configured to receive input from the user interface 144 and/or the sensors 146, and to control the actuators 152 and/or the recompression unit 110 based on the input. Furthermore, the controller 148 can be configured to receive input from the user interface 144 and/or the sensors 146 and to generate a display at the user interface 144 based on the input.

The sensors 146 can be configured to measure pressure, volume, temperature, mass flow rate, and/or other suitable parameters of refrigerant at one or more positions within the system 100. For example, individual sensors 146 can be operably coupled to the high-pressure line 106 and/or the low-pressure line 108 and configured to measure and/or monitor the first volume of refrigerant. Similarly, a sensor 146 can be operably connected to the make-up reservoir 138 and configured to measure and/or monitor the second volume of refrigerant. The controller 148 can be configured to receive an indication of refrigerant loss from the first volume of refrigerant and to open the make-up valve 140 (e.g., via an actuator 152) in response to the indication. The make-up valve 140 can be opened in a controlled manner (e.g., for a selected period of time and/or to a selected extent) to permit refrigerant from the second volume of refrigerant to flow into the first volume of refrigerant in a quantity sufficient to compensate for the detected refrigerant loss from the first volume of refrigerant.

In some cases, it can be useful for refrigerant supplied to the cryo-catheter 102 to be free or nearly free of moisture (e.g., liquid water and/or water vapor), particulates, and/or other contaminants. Moisture, for example, can freeze within the cryo-catheter 102 into ice particles, which, along with other types of particulates, can interfere with operation of the cryo-catheter 102. The system 100 can include a filter 154 configured to remove moisture, particulates, or both during refrigerant reprocessing. The filter 154 can be positioned at a point along the high-pressure line 106, at a point along the low-pressure line 108, or at another suitable position within the system 100. When the filter 154 is positioned at a point along the high-pressure line 106, the filter 154 can be configured to filter liquid refrigerant (e.g., to remove liquid-entrained particulates and/or liquid water). Similarly, when the filter 154 is positioned at a point along the low-pressure line 108, the filter 154 can be configured to filter gaseous refrigerant (e.g., to remove gas-entrained particulates and/or water vapor). In some embodiments, the filter 154 includes a molecular sieve (e.g., activated alumina) having a suitable pore size (e.g., 3A or 4A) alone or in combination with one or more other filtering components (e.g., an adsorbent material or a polymer membrane).

The portion of the closed loop defined by the high-pressure line 106, the low-pressure line 108, and the recompression unit 110 can be generally impermeable to moisture and/or refrigerant. For example, components within the console 104 configured to contain refrigerant can be constructed from generally moisture-impermeable and/or refrigerant-impermeable materials, such as certain metals or fluorinated polymers (e.g., polychlorotrifluoroethylene), and/or connected using generally moisture-impermeable and/or refrigerant-impermeable connections (e.g., welded connections). In some cases, the moisture permeability and/or refrigerant permeability of the supply lumen 112, the exhaust lumen 114, and/or other refrigerant-carrying components of the cryo-catheter 102 can be greater than the moisture permeability and/or refrigerant permeability of refrigerant-carrying components of the system 100 located within the console 104. The materials, construction techniques, and/or other features of the refrigerant-carrying components of the cryo-catheter 102, for example, can be selected to favor greater flexibility, lower cost, greater compactness, and/or other attributes over low moisture and/or refrigerant permeability. In some cases, the supply lumen 112 and the exhaust lumen 114 can be made of a polyimide or another suitable material with non-negligible moisture and/or refrigerant permeability. In other cases, components of the cryo-catheter 102 configured to contain refrigerant can be constructed from generally moisture-impermeable and/or refrigerant-impermeable materials, such as certain composites (e.g., metal-lined polymers) or fluorinated polymers (e.g., polychlorotrifluoroethylene).

The console 104 can be relatively durable and the cryo-catheter 102 can be at least partially disposable (e.g., after one, two, three, or another suitable number of treatments). Furthermore, in some embodiments, the console 104 is configured to store generally all refrigerant within the system 100 when the system 100 is not in use (e.g., overnight and/or between treatments) and/or when the cryo-catheter 102 is being replaced. In contrast, the cryo-catheter 102 can be configured to carry circulating refrigerant during a treatment, but, in some cases, not to store refrigerant before and after the treatment. Accordingly, refrigerant loss from the system 100 and/or introduction of moisture into the system 100 due to the moisture and/or refrigerant permeability of refrigerant-carrying components of the cryo-catheter 102 can be relatively low. The filter 154 and the make-up reservoir 138 can be configured, respectively, to remove this moisture contamination and to replace this refrigerant loss in addition, respectively, to removing moisture contamination and replacing refrigerant loss that can occur when the cryo-catheter 102 is detached from the console 104.

In some embodiments, the system 100 is configured to reduce or eliminate refrigerant loss associated with detaching the cryo-catheter 102 from the console 104. For example, the system 100 can be configured such that a relatively small percentage of refrigerant within the system 100 (e.g., a percentage from about 0.01% to about 5%, from about 0.1% to about 5%, from about 1% to about 5%, or within another suitable range) is within the cryo-catheter 102 at any given time. Thus, even if all refrigerant within the cryo-catheter 102 is lost when the cryo-catheter 102 is detached from the console 104, the percentage of lost refrigerant relative to total refrigerant within the system 100 can be relatively small. Furthermore, the console 104 can be configured to evacuate remaining refrigerant within the cryo-catheter 102 after a treatment. For example, after a treatment, the supply valve 134 can be closed and the recompression unit 110 can be used to draw out remaining refrigerant within the cryo-catheter 102. After the remaining refrigerant has been mostly or entirely evacuated, the exhaust valve 136 can be closed. The third coupler 120 can then be detached from the first coupler 116, the fourth coupler 122 can be detached from the second coupler 118, and the cryo-catheter 102 can be discarded. The system 100 can be configured to reduce or eliminate the intake of air into the high-pressure line 106 and the low-pressure line 108 during this process. Since air contains water vapor, this can be useful to help maintain refrigerant within the system 100 free or nearly free of moisture.

Figure 2:
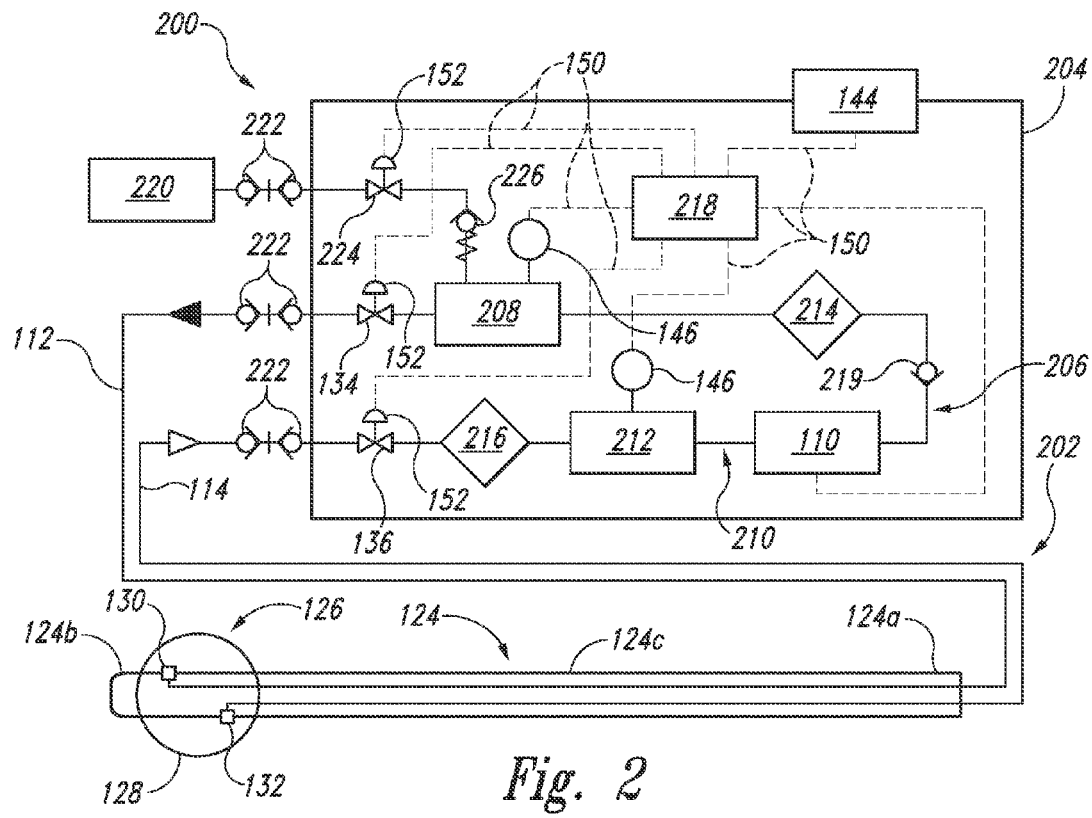

FIG. 2 is a partially schematic diagram illustrating a cryo-therapeutic system 200 in accordance with another embodiment of the present technology. The system 200 can include a cryo-catheter 202 removably connected to a console 204. Within the console 204, the system 200 can include a high-pressure line 206 having a supply vessel 208, and a low-pressure line 210 having an exhaust vessel 212. The supply vessel 208 and the exhaust vessel 212 can be configured to increase the refrigerant capacity of the high-pressure line 206 and the low-pressure line 210, respectively. This can be useful, for example, when the console 204 is configured to store the entirety or nearly the entirety of the refrigerant within the system 200 when the system 200 is not in use. In some embodiments, the high-pressure line 206 and the low-pressure line 210 have enhanced refrigerant capacity due to their length and/or diameter. For example, the high-pressure line 206 and the low-pressure line 210 can include serpentine portions (not shown) or coils (not shown) in place of or in addition to the supply vessel 208 and the exhaust vessel 212, respectively. In other embodiments, only the low-pressure line 210 can have enhanced refrigerant capacity and the system 200 can be configured to store refrigerant primarily before recompression. In still other embodiments, only the high-pressure line 206 can have enhanced refrigerant capacity and the system 200 can be configured to store refrigerant primarily after recompression.

With reference again to FIG. 2, the system 200 can include a high-pressure filter 214 at a suitable point along the high-pressure line 206 and a low-pressure filter 216 at a suitable point along the low-pressure line 210. The high-pressure filter 214 and the low-pressure filter 216 can be configured to remove moisture, particulates, or both during refrigerant reprocessing. In some embodiments, the high-pressure filter 214 and the low-pressure filter 216 are positioned upstream from the supply vessel 208 and the exhaust vessel 212, respectively. In other embodiments, the high-pressure filter 214 and the low-pressure filter 216 can be positioned downstream from the supply vessel 208 and the exhaust vessel 212, respectively.

The system 200 can include a controller 218 operably connected to the sensors 146, the actuators 152, the recompression unit 110, and the user interface 144. In some embodiments, the system 200 has more than one operational mode implemented by the controller 218 (e.g., in response to a user-initiated command from the user interface 144 and/or an indication from one or more of the sensors 146). For example, the system 200 can operate in a first mode during a treatment and in a second mode when the system 200 is not in use. In the first mode, the system 200 can be configured to at least partially deplete a supply of refrigerant within the supply vessel 208 by supplying refrigerant from the supply vessel 208 to the supply lumen 112. Also in the first mode, the system 200 can be configured to receive refrigerant within the exhaust vessel 212 from the exhaust lumen 114 via the low-pressure line 210. In the second mode, the system 200 can be configured to at least partially replenish the supply of refrigerant within the supply vessel 208 with refrigerant from the exhaust vessel 212 via the recompression unit 110.

The first and second modes can be non-concurrent. For example, the system 200 can be configured to operate in the second mode between treatments and/or overnight when operation of the recompression unit 110 is less likely to be disruptive (e.g., due noise associated with operation of the recompression unit 110). In other embodiments, the system 200 can be configured to supply high-pressure refrigerant to the supply lumen 112 and to recompress exhausted refrigerant from the exhaust lumen 114 concurrently. The exhaust vessel 212 can have a capacity sufficient to contain exhausted refrigerant from a limited number of treatments, such as one treatment or one cycle of treatments (e.g., from about one treatment to about 20 treatments or a number of treatments performed during a single day of treatments). When the supply vessel 208 is configured to contain liquid refrigerant and the exhaust vessel 212 is configured to contain gaseous refrigerant, it can be desirable to store surplus refrigerant (e.g., a quantity of refrigerant greater than a quantity of refrigerant used for one treatment or one cycle of treatments) within the supply vessel 208 rather than within the exhaust vessel 212. This can be the case, for example, because refrigerant can be unduly voluminous in the gas phase and relatively compact in the liquid phase. The system 200 can include a check valve 219 downstream from the recompression unit 110, which can be configured to reduce or prevent migration of refrigerant from the high-pressure line 206 to the low-pressure line 210 (e.g., when the recompression unit 110 is not active). In some embodiments, the check valve 219 is within the recompression unit 110. For example, a positive displacement pump (not shown) within the recompression unit 110 can serve as the check valve 219.

The system 200 can include a make-up reservoir 220 removably connectable to the closed loop (e.g., at the high-pressure line 206, at the low-pressure line 210, or at another suitable position within the closed loop). The make-up reservoir 220 can be disposable or configured to be disconnected from the high-pressure line 206 and refilled (e.g., at a remote facility) after it is depleted of refrigerant. The make-up reservoir 220 and high-pressure line 206 can include cooperative coupler valves 222. In some embodiments, the high-pressure line 206 includes another coupler valve 222 configured to releasably connect to a coupler valve 222 of the supply lumen 112. Similarly, the low-pressure line 210 can include a coupler valve 222 configured to releasably connect to a coupler valve 222 of the exhaust lumen 114. One or both members of one or more of the pairs of cooperative coupler valves 222 can be configured to automatically open when coupled to the corresponding member of the pair and to automatically close when not coupled to the corresponding member of the pair. Accordingly, some or all of the coupler valves 222 can act as check valves that reduce refrigerant loss and/or entry of air into components of the system 200 when the make-up reservoir 220 and/or the cryo-catheter 202 are partially or fully disconnected from the console 204. Thus, if the cryo-catheter 202 is temporarily disconnected from the console 204, the coupler valves 222 of the supply lumen 112 and the exhaust lumen 114 can reduce refrigerant loss from the cryo-catheter 202 even when remaining refrigerant within the cryo-catheter 202 is not displaced (e.g., as described above). This can be useful, for example, when the cryo-catheter 202 is reusable. The coupler valves 222 can be threaded, compression fit, barbed, or have other suitable cooperative features.

In some embodiments, the high-pressure line 206 includes a shutoff valve 224 and a pressure-regulated valve 226 configured to control the flow of refrigerant from the make-up reservoir 220 to the supply vessel 208 or to another portion of the high-pressure line 206 downstream from the make-up reservoir 220. In other embodiments, the make-up reservoir 220 can be removably connected to the system 200 at the low-pressure line 210, and the low-pressure line 210 can include the shutoff valve 224 and the pressure-regulated valve 226. With reference again to FIG. 2, the controller 218 can be configured to open the shutoff valve 224 after the system 200 at least partially replenishes the supply of refrigerant within the supply vessel 208 with refrigerant from the exhaust vessel 212 (e.g., while the system 200 is in the second operational mode). The pressure-regulated valve 226 can be configured to automatically open when a pressure within the supply vessel 208 is less than a threshold pressure. The threshold pressure can be selected to be at or near a pressure within the supply vessel 208 when the supply vessel 208 is full of refrigerant (e.g., when the supply vessel 208 contains refrigerant at full capacity or at another predetermined level). For example, when the system 200 is in the second operational mode and has completed replenishing the supply of refrigerant within the supply vessel 208, if the supply vessel 208 is not full, the pressure within the supply vessel 208 can be less than the threshold pressure causing the pressure-regulated valve 226 to open until the supply vessel 208 is refilled by the influx of refrigerant from the make-up reservoir 220.

Figure 3:
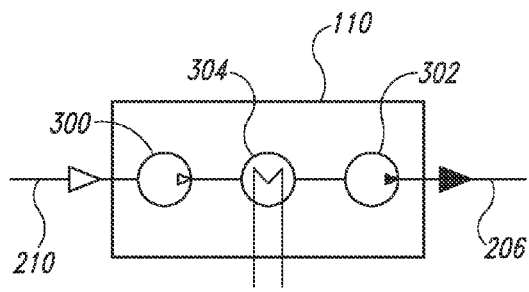
FIG. 3 is an enlarged, partially schematic diagram illustrating a recompression unit of the cryotherapeutic system shown in FIG. 2.

FIG. 3 is an enlarged, partially schematic diagram illustrating the recompression unit 110 along with adjacent portions of the high-pressure line 206 and the low-pressure line 210. The recompression unit 110 can be configured to increase the pressure of refrigerant from the low-pressure line 210 to the high-pressure line 206. In some cases, refrigerant within the high-pressure line 206 downstream from recompression unit 110 can be at a treatment pressure (e.g., a cryo-treatment pressure sufficient for cryogenic alteration of tissue). For example, the recompression unit 110 can be configured to increase the pressure of refrigerant from the low-pressure line 210 to a treatment pressure of about 700 psi to about 900 psi in the high-pressure line 206 when the recompression unit 110 is configured for use with room-temperature nitrous oxide. As another example, the recompression unit 110 can be configured to increase the pressure of refrigerant from the low-pressure line 210 to a treatment pressure of about 300 psi to about 500 psi in the high-pressure line 206 when the recompression unit 110 is configured for use with chilled nitrous oxide. As yet another example, the recompression unit 110 can be configured to increase the pressure of refrigerant from the low-pressure line 210 to a treatment pressure of about 200 psi to about 300 psi in the high-pressure line 206 when the recompression unit 110 is configured for use with a hydrofluorocarbon refrigerant.

In some embodiments, the recompression unit 110 is configured to at least partially condense refrigerant moving through the recompression unit 110. The recompression unit 110 can include a first pump 300, a second pump 302, and a condenser 304 therebetween. The first pump 300 can be configured to pump gaseous refrigerant. For example, the first pump 300 can be configured to draw exhausted refrigerant into the recompression unit 110 and/or to raise the pressure of exhausted refrigerant to a pressure slightly below the saturation pressure of the type of refrigerant at room temperature or at an operating temperature of the recompression unit 110. The condenser 304 can be configured to at least partially condense refrigerant downstream from the first pump 300 (e.g., by extracting heat from refrigerant passing through the condenser 304). The second pump 302 can be a condensate pump configured to pump liquid refrigerant. For example, the second pump 302 can be configured to pressurize condensed refrigerant exiting the condenser 304 to at least a treatment pressure and to control the flow of refrigerant away from the recompression unit 110. In some cases, the second pump 302 can be a positive displacement pump configured to prevent backflow through the recompression unit 110.

Figure 4:
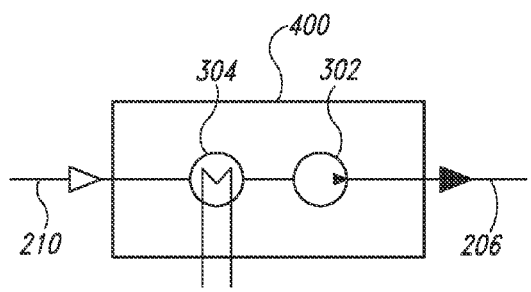
FIGS. 4-7 are enlarged, partially schematic diagrams illustrating recompression units in accordance with additional embodiments of the present technology.
Figure 5:
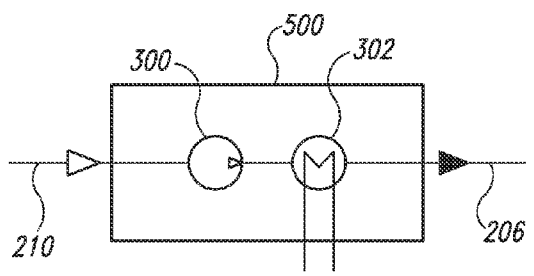
Figure 6:
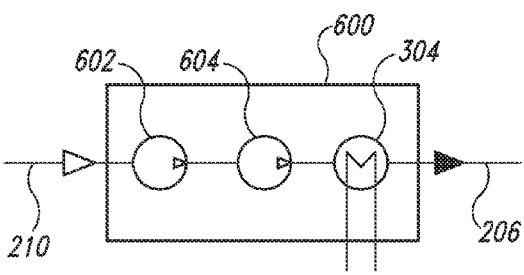

Many variations of the recompression units 110, 400 are possible in accordance with embodiments of the present technology. For example, the first pump 300, the second pump 302, and/or the condenser 304 individually can include one or more stages. In some embodiments, the first pump 300, the second pump 302, and the condenser 304 have another suitable order within the recompression unit 110. Furthermore, the first pump 300, the second pump 302, or the condenser 304 can be eliminated. FIG. 4 is an enlarged, partially schematic diagram illustrating a recompression unit 400 including the condenser 304 and the second pump 302 without the first pump 300. FIG. 5 is an enlarged, partially schematic diagram illustrating a recompression unit 500 including the first pump 302 and the condenser 304 without the second pump 302. FIG. 6 is an enlarged, partially schematic diagram illustrating a recompression unit 600 including the condenser 304, a first-stage pump 602 upstream from the condenser 304, and a second-stage pump 604 between the condenser 304 and the first-stage pump 602. In the recompression units 500, 600, the first pump 300, the first-stage pump 602, and the second-stage pump 604 can be configured to pump gaseous refrigerant.

Figure 7:
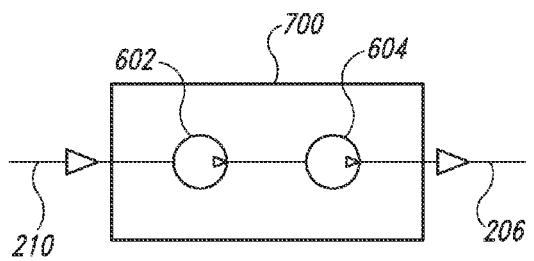

FIG. 7 is an enlarged, partially schematic diagram illustrating a recompression unit 700 that is not configured to condense refrigerant. The recompression unit 700 can include the first-stage pump 602 and the second-stage pump 604 downstream from the first-stage pump 602. In other embodiments, the recompression unit 700 can be configured for only one refrigerant recompression stage or for more than two refrigerant recompression stages. With reference to FIGS. 3-7 together, the recompression units 110, 400, 500, 600, 700 can be configured to increase the pressure of refrigerant moving from the low-pressure line 210 to the high-pressure line 206 by a ratio from about 1:5 to about 1:75 (e.g., a ratio from about 1:10 to about 1:50). In some embodiments, the recompression units 110, 400, 500, 600, 700 are configured to increase the pressure of refrigerant moving from the low-pressure line 210 to the high-pressure line 206 by a ratio of at least 1:30 (e.g., at least 1:50).

Figure 8:
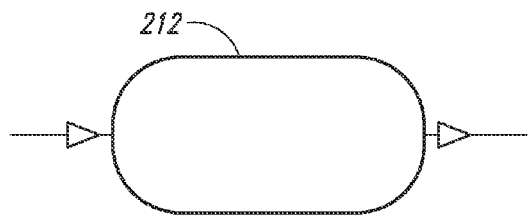
FIG. 8 is an enlarged, partially schematic diagram illustrating an exhaust vessel of the cryotherapeutic system shown in FIG. 2.
Figure 9:
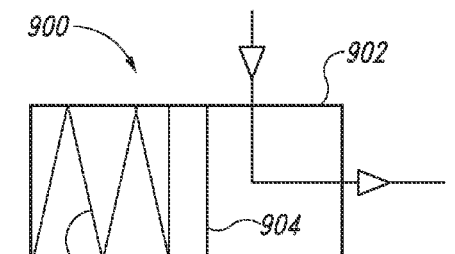
FIGS. 9 and 10 are enlarged, partially schematic diagrams illustrating exhaust vessels in accordance with additional embodiments of the present technology.
Figure 10:
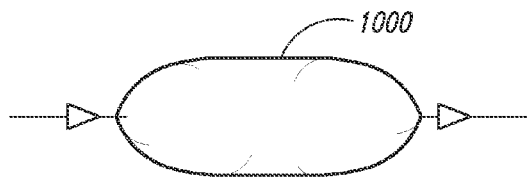

FIG. 8 is an enlarged, partially schematic diagram illustrating the exhaust vessel 212 (FIG. 2), which can be a fixed-volume tank. In other embodiments, the exhaust vessel 212 can be expandable, which can reduce the presence of air within the exhaust vessel 212 and/or other refrigerant-carrying component of the system 200. For example, FIG. 9 is a enlarged, partially schematic diagram illustrating an exhaust vessel 900 including a cylinder 902, a piston 904 within the cylinder 902, and a biasing member 906 configured to resiliently retract the piston 904 when refrigerant is introduced into the exhaust vessel 900. As another example, FIG. 10 is an enlarged, partially schematic diagram illustrating an exhaust vessel 1000 that is an inflatable bladder, which can be configured to expand compliantly, non-compliantly, or semi-compliantly when refrigerant is introduced into the exhaust vessel 1000. With reference to FIG. 2, expanding the exhaust vessel 212 can facilitate temporary storage of refrigerant upstream from the recompression unit 110 (e.g., before activating the recompression unit 110 during the second operational mode). In some embodiments, the supply vessel 208 is expandable in addition to or instead of the exhaust vessel 212 being expandable. For example, the supply vessel 208 can have one of the forms described above with reference to FIGS. 9 and 10.

Figure 11:
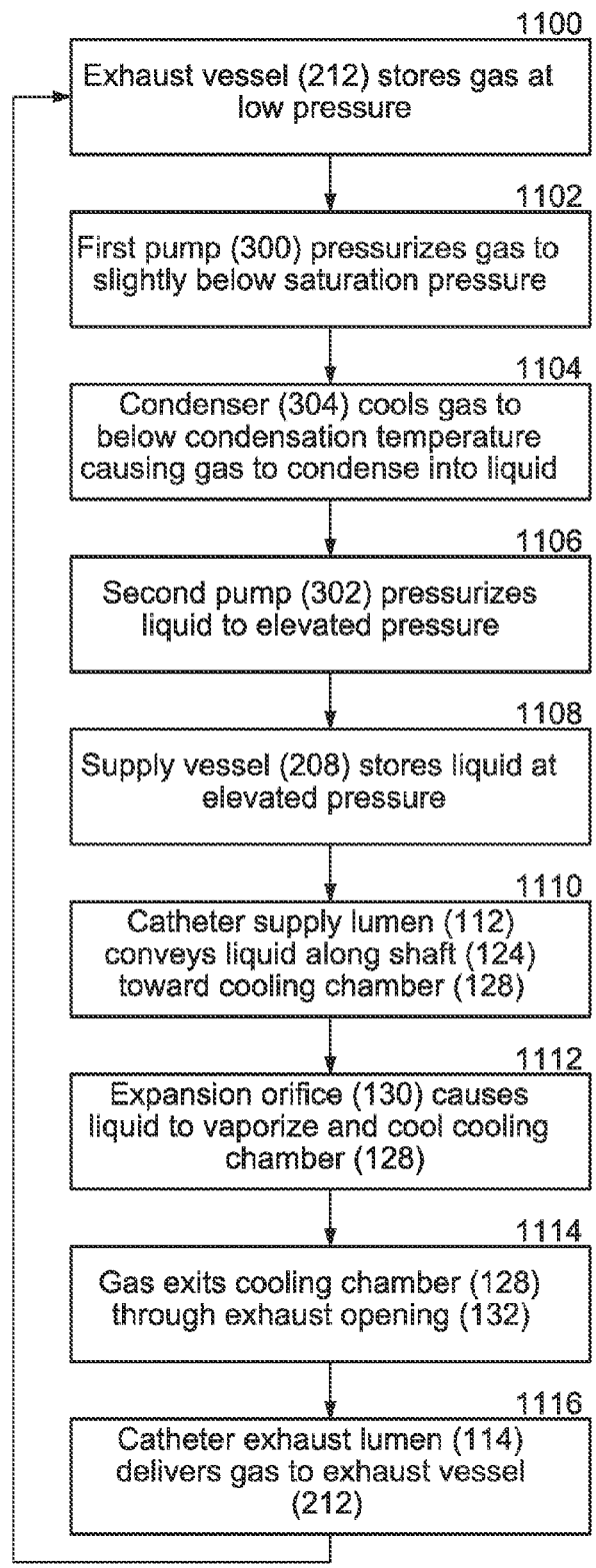
FIG. 11 is a block diagram illustrating stages during operation of the cryotherapeutic system shown in FIG. 2 in accordance with an embodiment of the present technology.

FIG. 11 is a block diagram illustrating stages during operation of the system 200 in accordance with an embodiment of the present technology. The stages can occur simultaneously (e.g., during steady-state operation of the system 200) or non-simultaneously (e.g., during start-up and/or shut-down of the system 200). With reference to FIGS. 2, 3 and 11 together, at a first stage 1100, a volume of refrigerant within the system 200 can be contained in the exhaust vessel 212 as a gas at a relatively low pressure (e.g., a pressure slightly above atmospheric pressure). At a second stage 1102, the first pump 300 can pressurize the refrigerant (e.g., to a pressure slightly below its saturation pressure at room temperature). At a third stage 1104, the condenser 304 can cool the refrigerant to a temperature below its condensation temperature. This cooling can cause the refrigerant to condense into a liquid. At a fourth stage 1106, the second pump 302 can pump the refrigerant to a pressure high enough to maintain circulation through the system 200.

At a fifth stage 1108, the refrigerant can be contained in the supply vessel 208 as a liquid at a relatively high pressure. In some cases, make-up refrigerant can be added to the supply vessel 208 to replace any refrigerant loss from the system 200. At a sixth stage 1110, the refrigerant can travel through the supply lumen 112 to the expansion orifice 130. The pressure of the refrigerant within the supply vessel 208 can be sufficiently high to generally maintain the refrigerant in liquid phase while it travels to the expansion orifice 130. At a seventh stage 1112, the refrigerant can travel through the expansion orifice 130 and into the cooling chamber 128. A sharp drop in pressure at the expansion orifice 130 can cause the refrigerant to vaporize, which can cool the cooling chamber 128 primarily due to the refrigerant absorbing its latent heat of vaporization. At an eighth stage 1114, the refrigerant in gaseous phase can exit the cooling chamber 128 via the exhaust opening 132. At a ninth stage 1116, the refrigerant can travel though the exhaust lumen 114 to the exhaust vessel 212. The refrigerant can then repeat the process beginning with the first stage 1100 if the system 200 is still in use or remain in the exhaust vessel 212 until the system 200 is restarted.

This disclosure is not intended to be exhaustive or to limit the present technology to the precise forms disclosed herein. Although specific embodiments of the present technology are disclosed herein for illustrative purposes, various equivalent modifications are possible without deviating from the present technology, as those of ordinary skill in the relevant art will recognize. In some cases, well-known structures and/or functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. While advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the present technology. This disclosure and the associated technology encompass a wide variety of other embodiments not expressly shown or described herein.

Certain aspects of the present technology may take the form of computer-executable instructions, including routines executed by a controller or other data processor. In some embodiments, a controller or other data processor is specifically programmed, configured, or constructed to perform one or more of these computer-executable instructions. Furthermore, some aspects of the present technology may take the form of data (e.g., non-transitory data) stored or distributed on computer-readable media, including magnetic or optically readable or removable computer discs as well as media distributed electronically over networks. Data structures and transmissions of data particular to aspects of the present technology are encompassed within the scope of the present technology. The present technology also encompasses methods of both programming computer-readable media to perform particular steps and executing the steps.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "including," "comprising" and the like are used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various structures. It should be understood that such terms do not denote absolute orientation. Reference herein to "one embodiment," "an embodiment," or similar formulations means that a particular feature, component, or operation described in connection with the embodiment can be included in at least one embodiment of the present technology. Thus, the appearances of such phrases or formulations herein are not necessarily all referring to the same embodiment. Furthermore, various particular features, components, and/or operations may be combined in any suitable manner based on this disclosure.

We claim:

1. A cryotherapeutic system, comprising:
   a high-pressure line configured to be removably connected to a supply lumen of a cryo-catheter;
   a low-pressure line configured to be removably connected to an exhaust lumen of the cryo-catheter;
   a recompression unit operably connected to the high-pressure line and the low-pressure line, the recompression unit being configured to increase the pressure of and at least partially condense refrigerant moving from the low-pressure line to the high-pressure line, wherein the high-pressure line, the low-pressure line, and the recompression unit are configured to contain a first volume of refrigerant; and
   a make-up reservoir configured to contain a second volume of refrigerant sufficient to replace refrigerant loss from the first volume of refrigerant caused by disconnecting the supply lumen from the high-pressure line, disconnecting the exhaust lumen from the low-pressure line, or both,
   wherein the high-pressure line, the low-pressure line, and the recompression unit are configured to define a portion of a closed loop when the high-pressure line is operably connected to the supply lumen and the low-pressure line is operably connected to the exhaust lumen.

2. The system of claim 1, wherein the make-up reservoir is removably connectable to the high-pressure line, the low-pressure line, or both.

3. The system of claim 1, further comprising the cryo-catheter, wherein the cryo-catheter includes:
   a shaft within which the supply lumen and the exhaust lumen are disposed; and
   a cryo-applicator attached to the shaft, the cryo-applicator having a cooling chamber configured to receive refrigerant from the high-pressure line via the supply lumen and to return refrigerant to the low-pressure line via the exhaust lumen.

4. The system of claim 3, wherein the cryo-catheter is disposable.

5. A cryotherapeutic system, comprising:
   a high-pressure line configured to be removably connected to a supply lumen of a cryo-catheter, the high-pressure line including a supply vessel configured to contain liquid refrigerant;
   a low-pressure line configured to be removably connected to an exhaust lumen of the cryo-catheter, the low-pressure line including an exhaust vessel configured to contain gaseous refrigerant; and
   a recompression unit operably connected to the high-pressure line and the low-pressure line, the recompression unit being configured to increase the pressure of and at least partially condense refrigerant moving from the low-pressure line to the high-pressure line,
   wherein the high-pressure line, the low-pressure line, and the recompression unit are configured to define a portion of a closed loop when the high-pressure line is operably connected to the supply lumen and the low-pressure line is operably connected to the exhaust lumen.

6. The system of claim 5, wherein the exhaust vessel is expandable.

7. The system of claim 5, wherein:
   the system has a first operational mode and a non-concurrent second operational mode;
   the system is configured to at least partially deplete a supply of refrigerant within the supply vessel by supplying refrigerant from the supply vessel to the supply lumen when the high-pressure line is operably connected to the supply lumen and the system is in the first operational mode; and
   the system is configured to at least partially replenish the supply of refrigerant within the supply vessel with refrigerant from the exhaust vessel while the system is in the second operational mode.

8. The system of claim 7, wherein:
   the high-pressure line, the low-pressure line, and the recompression unit are configured to contain a first volume of refrigerant; and
   the system further comprises—
      a make-up reservoir configured to contain a second volume of refrigerant sufficient to replace refrigerant loss from the first volume of refrigerant caused by disconnecting the supply lumen from the high-pressure line, disconnecting the exhaust lumen from the low-pressure line, or both, and a make-up valve operably connected to the make-up reservoir, the make-up valve configured to regulate movement of refrigerant from the second volume of refrigerant toward the first volume of refrigerant.

9. The system of claim 8, further comprising:
a pressure sensor, a volume sensor, or both configured to detect refrigerant loss from the first volume of refrigerant; and
a controller configured to receive an indication of refrigerant loss from the pressure sensor, the volume sensor, or both, and to open the make-up valve in response to the indication.

10. The system of claim 8, wherein:
the make-up reservoir and the make-up valve are operably connected to the high-pressure line;
the make-up valve is a pressure-regulated valve configured to automatically open when a pressure within a portion of the high-pressure line downstream from the pressure-regulated valve is less than a threshold pressure; and
the system further comprises a shutoff valve operably connected to the make-up reservoir and the high-pressure line.

11. The system of claim 10, further comprising a controller configured to open the shutoff valve after the system at least partially replenishes the supply of refrigerant within the supply vessel with refrigerant from the exhaust vessel while the system is in the second operational mode.

12. The system of claim 10, wherein the threshold pressure is selected to be at or near a pressure within the supply vessel when the supply vessel is full of refrigerant.

13. The system of claim 5, further comprising the cryo-catheter, wherein the cryo-catheter includes:
a shaft within which the supply lumen and the exhaust lumen are disposed; and
a cryo-applicator attached to the shaft, the cryo-applicator having a cooling chamber configured to receive refrigerant from the high-pressure line via the supply lumen and to return refrigerant to the low-pressure line via the exhaust lumen.

14. The system of claim 5, wherein the recompression unit is a single-stage pump configured to increase the pressure of refrigerant from the low-pressure line to the high-pressure line by a ratio of at least 1:50.

15. The system of claim 5, wherein the recompression unit is a multi-stage pump configured to increase the pressure of refrigerant from the low-pressure line to the high-pressure line by a ratio of at least 1:50.

16. The system of claim 1, wherein the cryo-catheter is disposable.

17. The system of claim 5, further comprising a reservoir fluidically coupled to the high-pressure line, the low-pressure line, the recompression unit, or a combination thereof, wherein the high-pressure line, the low-pressure line, and the recompression unit are configured to contain a first volume of refrigerant, and the reservoir is configured to contain a second volume of refrigerant sufficient to replace refrigerant loss from the first volume of refrigerant.

18. The system of claim 17, further comprising a controller operably coupled to the reservoir, wherein the controller includes instructions to inject refrigerant from the second volume of refrigerant in the reservoir to the first volume of refrigerant.

19. The system of claim 5, further comprising a filter fluidically coupled to the high-pressure line, the low-pressure line, the recompression unit, or a combination thereof, wherein the filter is configured to remove moisture, particulates, or both from refrigerant within the system.

20. The system of claim 5, wherein the recompression unit is configured to increase the pressure of refrigerant moving from the low-pressure line to the high-pressure line by a ratio from about 1:5 to about 1:75.

21. The system of claim 5, wherein the recompression unit includes a condenser and a positive displacement pump downstream from the condenser.

22. The system of claim 5, wherein:
the high-pressure line includes a supply valve configured to change the flow of refrigerant toward the supply lumen;
the low-pressure line includes an exhaust valve configured to change the flow of refrigerant toward the recompression unit; and
the system further comprises a controller operably connected to the exhaust valve and the supply valve.

23. The system of claim 5, wherein the portion of the closed loop is generally impermeable to moisture.

24. The system of claim 5, wherein:
the high-pressure line includes a first coupler valve configured to automatically open when the high-pressure line is operably connected to the supply lumen and to automatically close when the high-pressure line is not operably connected to the supply lumen; and
the low-pressure line includes a second coupler valve configured to automatically open when the low-pressure line is operably connected to the exhaust lumen and to automatically close when the low-pressure line is not operably connected to the exhaust lumen.

25. The system of claim 5, further comprising a check valve within or downstream from the recompression unit, the check valve configured to reduce or prevent migration of refrigerant from the high-pressure line to the low-pressure line.

* * * * *